United States Patent [19]
Yang

[11] Patent Number: 4,883,898
[45] Date of Patent: Nov. 28, 1989

[54] CHEMILUMINESCENT COMPOUNDS

[75] Inventor: Nien-chu C. Yang, Chicago, Ill.

[73] Assignee: University of Chicago, Chicago, Ill.

[21] Appl. No.: 131,113

[22] Filed: Dec. 10, 1987

[51] Int. Cl.[4] .................... C07C 69/76; C07C 63/33; C09K 11/00
[52] U.S. Cl. ..................... 558/427; 560/80; 562/488; 252/700
[58] Field of Search ............... 560/80, 102; 562/488; 558/427; 252/700

[56] References Cited

U.S. PATENT DOCUMENTS

| | | | |
|---|---|---|---|
| 3,489,791 | 1/1970 | Ciganek | 558/427 |
| 3,720,701 | 3/1973 | Klanderman et al. | 560/80 |
| 4,123,219 | 10/1978 | Sasse et al. | 560/80 |

OTHER PUBLICATIONS

Quast, et al. "Bridgehead Azides 5 . . . ", Liebigs Ann. Chem. 1985, 696–707.
Smothers, et al. "Photcycloaddition . . . ", J. Am. Chem. Soc. 1983, 105, 545–555.
Hemetsberger, et al., "Photochemical Deuterium . . . ", Tetrahedron, vol. 38, No. 9 pp. 1175–1182, 1982.
Wang, et al. "Photorearrangement", Tetrahedron Letters, vol. 23, No. 12, pp. 1231–1234, 1982.
Yang, et al "Chemistry of Exciplexes", Tetrahedron vol. 37, No. 19 pp. 3285–3300, 1981.
Kaupp et al "Primary Products in Photocycloadditions", Chem. Ber. 114(4) 1567–1571, 1981.
Kitamura, et al. "A Synthesis", Tetrahedron 36 (9) 1183–1189, 1980.
Kawada, et al. "A Novel Route From Triptycenes", Tetrahedron Lett. vol. 21, pp. 181–182, 1980.
Kitamura, "A New Synthesis", Tetrahedron Lett (44) 4297–4300, 1978.
Kaupp, "Photo-Diels-Alder", Justis Liebigs Ann. Chem. (2) 254–275, 1977.
Iwamura et al., "Photochemical Rearrangement", Chemistry Letters, pp. 1045–1048, 1976.
Iwamura, et al. "Novel Photorearrangement", J.C.S. Chem. Comm. 1975, 969–970.
Applequist, et al. "Anthracene Dimers . . . ", Jan. 20, 1959 p. 457, Anthracene Photodimers.

N. C. Yang, et al., A New Type of Pericyclic Chemiluminescence, J. Am. Chem. Soc. 109:3804–3805, 1987.
Ward, et al., Luminescent Materials, In: Encyclopedia of Chemical Technology, 3rd ed. vol. 14, pp. 527–569 (1981), Kirk-Othmer, Eds.
Denis J. Bogan, Gas-Phase Dioxetane Chemiluminescence, In: Chemical and Biological Generation of Excited States, Ch. 2, pp. 37,78–79 (1982), Adam & Cilento, Eds.
N. C. Yang, Chemistry of Benzene-Anthracene Cyclodimers, J. Am. Chem. Soc., vol. 106, No. 24, pp. 7310–7315, 1984.
Karl R. Kopecky, Synthesis of 1,2-Dioxetanes, In: Chemical and Biological Generation of Excited States, Ch. 3, pp. 85,99 (1982), Adam & Cilento, Eds.
Turro & Ramamurthy, Rearrangements in Ground and Excited States, In: Chemical Generation of Excited States, vol. 3, pp. 15–17 (1980), Paul de Mayo, Ed.
J. A. Yang, Chemistry of Benzene-Anthracene Cyclodimers, Chem. Soc. 104:953 (1982).

*Primary Examiner*—John F. Terapane
*Attorney, Agent, or Firm*—Leydig, Voit & Mayer

[57] ABSTRACT

A new class of chemiluminescent compounds is described which has the ability to emit light which corresponds to the fluorescence of the compounds' breakdown products. This chemiluminescence is stimulated by the energetic decomposition of the chemiluminescent compound. These chemiluminescent compounds have the following structure:

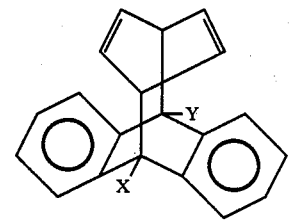

wherein X is hydrogen or an electron-withdrawing group; and Y is hydrogen or an electron-withdrawing group and both X and Y are not hydrogen.

13 Claims, 3 Drawing Sheets

6 + 3 → 4c hγ/uranyl / CH$_2$Cl$_2$, 0°C

8 → 5c

KOBu$^t$/H$_2$O / THF

9 → 1c

KDA / THF, 0°F

1c → 1e

CH$_2$N$_2$/Et$_2$O / THF, 0°C

CHEMILUMINESCENT COMPOUNDS

FIELD OF THE INVENTION

The present invention relates generally to a class of chemiluminescent compounds which has the ability to emit light during decomposition. This chemiluminescence is a direct conversion of chemical energy into light energy.

BACKGROUND OF THE INVENTION

The phenomenon known as chemiluminescence involves the conversion of chemical energy into light energy. Chemiluminescence is involved in many chemical and biological processes, such as the bioluminescence of the firefly utilizing the enzymatic system containing luciferin and luciferase; however, the nature of this reaction is not well understood. Most of the chemiluminescent systems known to date involve the decomposition of peroxides. Peroxides are dangerous compounds which often decompose explosively. Therefore, there is a need for chemiluminescent compounds which do not decompose explosively. Luminescence is broadly defined as the emission of electromagnetic radiation. Some luminescent materials are called phosphors. While there are literally thousands of known phosphors, less than 100 are commercially manufactured on a large scale. Some phosphors are used in fluorescent lamps and others are used in speciality applications, such as cathode ray screens. Phosphors may be excited by infrared radiation, electric fields, chemical reactions and mechanical stress. However, most phosphors are excited by high energy photons or electrons.

The best known thermal decomposition of a pericyclic chemiluminescent reaction is that of the Dewar benzenes as described by N. J. Turro and V. Ramamurphy in "Rearrangements in Ground and Excited States," Vol. 3, Academic Press, New York, 1980, p. 15. However, in this case, the luminescence observed was not derived from the product itself, but from an added sensitizer, that is, these are sensitized chemiluminescent reactions. There is no known direct pericyclic chemiluminescent reaction of homocyclic compounds in the scientific literature. By this we mean that the thermal dissociation of heterocyclic compounds, such as dioxetanes, to generate n,π* state involves the participation of n-orbitals and is not a chemiluminescent reaction of homocyclic compounds. The compounds of the present invention are homocyclic chemiluminescent compounds distinct from traditional phosphors and heterocyclic chemiluminescence.

The synthesis of benzene:anthracene cyclodimers shown below, results in a compound which exhibits reasonable stability under ordinary laboratory conditions. Yang, et al., J. Am. Chem. Soc., 104:953 (1982). The retrocycloaddition of the compound shown below (1a) results in two aromatic products rather than one and a decomposition which is not chemiluminescent.

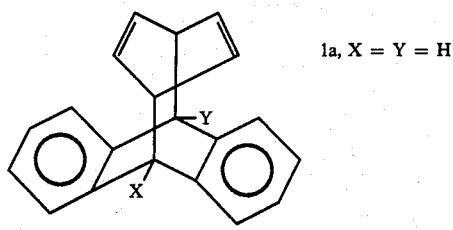

1a, X = Y = H

Potentially these energy rich pericyclic benzene:anthracene cyclodimers, such as 1 a contain sufficient energy and are sufficiently stable to function as a source of chemical energy for the development of an efficient unimolecular chemiluminescent system. However, there is a need to develop modified structures which actually exhibit chemiluminescence. A system based on such modified structures would have applications in the development of an organic chemical lasing system or in any system requiring a chemical source of light.

SUMMARY OF THE INVENTION

Described are the production and use of chemiluminescent compounds having the following composition:

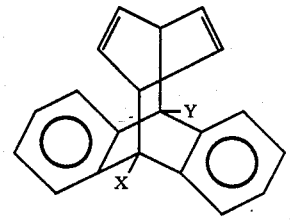

wherein X is hydrogen or an electron-withdrawing group; and Y is hydrogen or an electron-withdrawing group; and no more than one of X and Y are hydrogen.

Compounds of the present invention are chemiluminescent resulting in the conversion of chemical energy into light energy during decomposition. These and other features and advantages of the invention will be more readily apparent upon reading the following detailed description of the preferred embodiment of the invention and upon reference to the accompanying drawings.

DETAILED DESCRIPTION OF THE PREFERRED EMBODIMENT

The synthesis of benzene:anthracene cyclodimers bearing electronegative substitutions at the bridgehead positions X and Y results in the production of compounds which are chemiluminescent. Illustrated below are benzene:anthracene cyclodimers with the bridgehead positions X and Y as indicated.

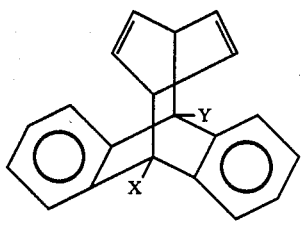

1a, X = Y = H
1b, X = COOH, Y = H
1c, X = Y = COOH
1d, X = CH$_3$, Y = H
1e, X = Y = COOCH$_3$

Compounds 1a through 1e have the following scientific nomenclature:

1a: 7,8,9,10-dibenzotricyclo[4.2.2.2$^{2,5}$]dodeca-3,7,9,11-tetraene;

1b: 7,8,9,10-dibenzotricyclo[4.2.2.2$^{2,5}$]dodeda-3,7,9,11-tetraene-1-carboxylic acid;

1c: 7,8,9,10-dibenzotricyclo[4.2.2.2$^{2,5}$]dodeca-3,7,9,11-tetraene-1,6-dicarboxylic acid;

1d: 1-methyl-7,8,9,10-dibenzotricyclo-[4.2.2.2$^{2,5}$]dodeca-3,7,9,11-tetraene;

1e: dimethyl 7,8,9,10-dibenzotricyclo-[4.2.2.2$^{2,5}$]dodeca-3,7,9,11-tetraene-1,6-dicarboxylate.

Figure 2:
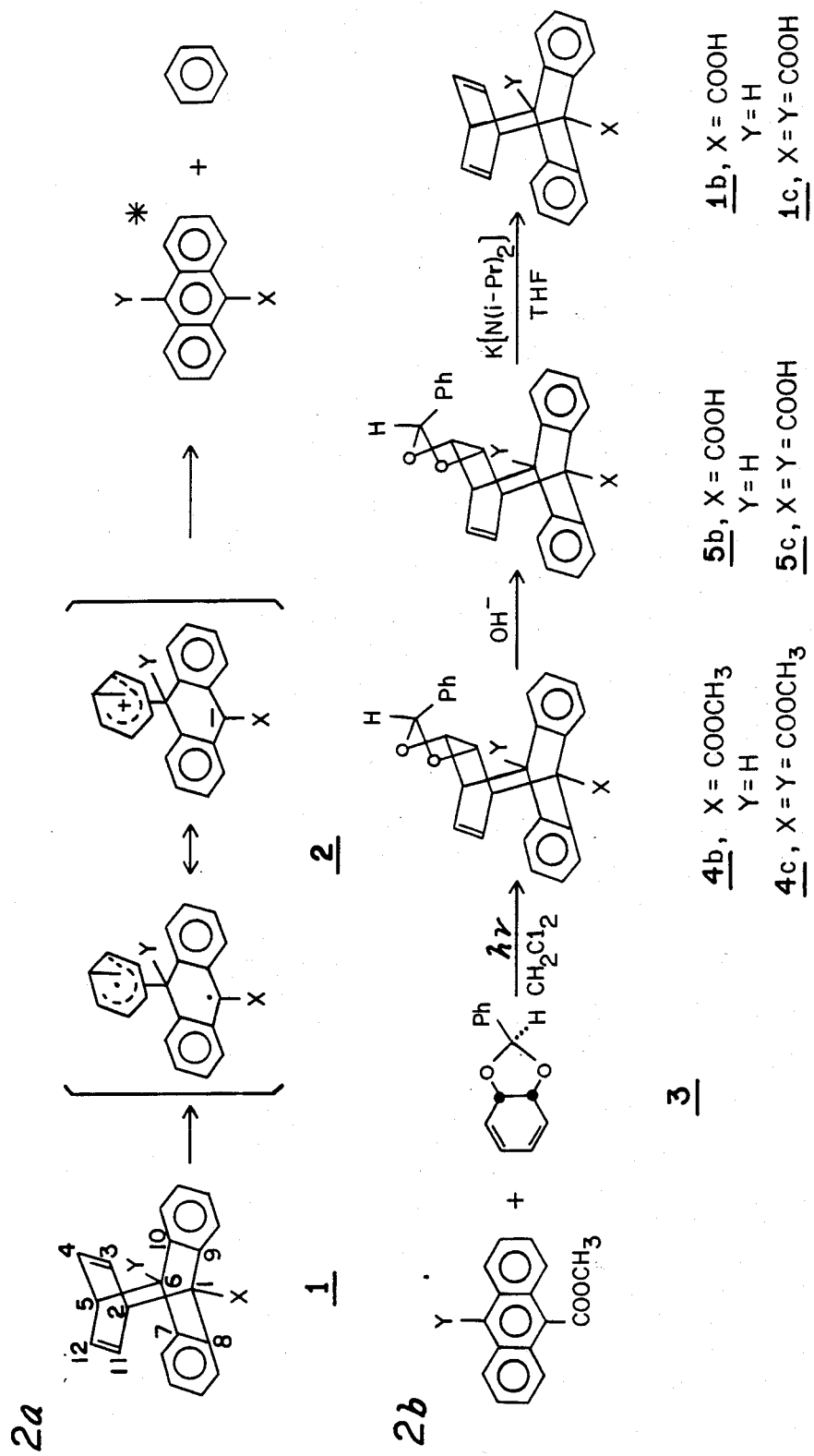
FIG. 2a is an equation illustrating an appropriate substituent at the bridge head position, such as an electronegative substituent at the 9 position of the anthryl moiety wherein the substituent introduces a polar character into compound 2 thereby facilitating a chemiluminescent reaction.
FIG. 2b is an equation illustrating the synthesis of compounds 1b and 1c.

Compounds 1b, 1c and 1e are chemiluminescent. Chemiluminescence results from the formation of excited state molecules. The production of these excited state molecules is governed by both an energy factor and by a probability factor. There must be sufficient energy available from the chemical reaction that it exceeds the excitation energy of the luminescent product. In addition, there must be a pathway or mechanism for the product in gaining access to the excited state. Dimers of benzene and anthracene which contain hydrogen or methyl groups at positions X and Y are not chemiluminescent in spite of the fact that the available energy exceeds the excited energy of anthracene. Yang, et al., J. Amer. Chem. Soc., 106, 7310-15 (1984). However, if the substitutions at the bridgehead position X or Y contain an electronegative substituent at this 9-position of the anthryl moiety, then it introduces a polar character as illustrated in FIG. 2a, compound 2. An electron withdrawing group is any molecule or group of molecules which exhibits electronegativity, which is a tendency to remove electrons more than hydrogen.

The partial anionic character of the anthryl moiety caused by the electronegative substituent may then proceed further along a reaction pathway which ultimately leads to the formation of a radical ion pair of a benzene radical cation and an anthracene radical ion. This pathway becomes endoergic as these ions separate to overcome the electrostatic attraction between them. Excited anthracene can be formed efficiently from excited compound 1 in a symmetry allowed and highly exoergic process. (Yang, et al., J. Amer. Chem. Soc., 106, 7310-5 [1984].)

The addition of electron-donor substitutients, such as alkoxy or siloxy, on the upper benzene ring will further enhance the charge separation of the compounds of the present invention. This simultaneous addition of electron-donors on the upper benzene and the electron-withdrawing groups at the X and/or Y positions of compound 1, will enhance the charge separation during the decomposition and thereby facilitate chemiluminescence.

The compounds of the present invention are chemiluminescent during decomposition. The preferred method for triggering the decomposition is heating. However, any method suitable for increasing the available energy is suitable for triggering the decomposition reaction and causing the emission of light. This energetic activation of the compounds of the present invention may be accomplished by utilizing any source of energy selected from the group consisting of thermal, infrared, radiant, nuclear, electrical or chemical sources.

Figure 1:
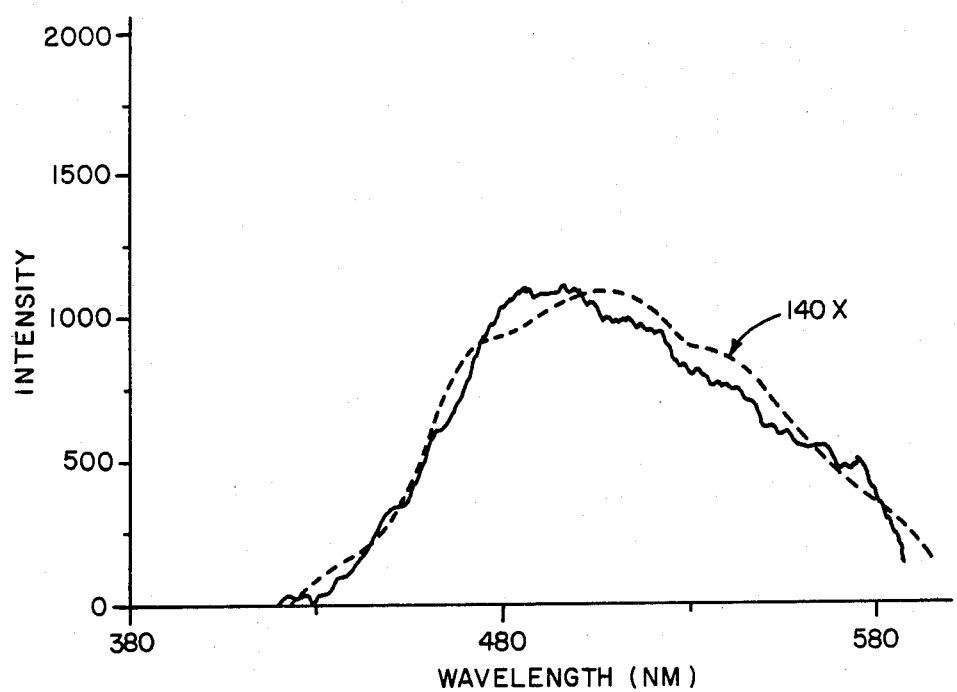
FIG. 1 illustrates the chemiluminescent spectrum of compound 1b at 150° C. (---) and the fluorescent spectrum of solid 9-anthroic acid at 125° C.

The synthesis of compounds 1b and 1c is illustrated in the equation in FIG. 2a. A spectroanalysis was obtained for all the intermediates and for compounds 1b-1d. However, an elemental analysis for the compounds 1b-1d was not attempted because of their low thermal stability. The gap between the energy level of the radical ion state of compound 1b and that of excited 9-anthroic acid was estimated from polarographic measurements utilizing the method of Pysh, et al., J. Amer. Chem. Soc., 85, 2124-30 (1963), and was found from spectrographic data to be approximately 15 kcal/mole. The thermolysis of these compounds in the solid state was distinctively chemiluminescent with the luminescence yield estimated to be less than 0.001. The chemiluminescence spectrum of the thermolysis of compound 1b was found to be virtually identical to the fluorescent spectrum of 9-anthroic acid as illustrated in FIG. 1.

Since the fluorescent state of 9-anthroic acid (0→0 band at 388 nm) is red-shifted from that of anthracene (0→0 band at 376 nm), the formation of an excited anthroic acid in the thermolysis of compound 1b could have been due to a more favorable energy factor. To disprove this, compound 1d carrying an electron-releasing methyl group was prepared utilizing the method of Yang, et al., J. Amer. Chem. Soc., 106, 7315-5 (1984). The thermolysis of compound 1d yielded 9-methyl anthracene which exhibited a fluorescent state (0→0 band at 388 nm) which was isoenergetic with that of 9-anthroic acid. However, the result of the thermolysis of compound 1d was not detectably different from that of compound 1a. Therefore, in contrast to an electronegative group an electron-releasing methyl group at the same position exerted no detectable effect to increase the probability of chemiluminescence of the parent compound.

The actual amount of energy required to form a 9-methylanthracene radical cation and the benzene radical anion may be extrapolated from the polarographic oxidation potential of 9-methylanthracene and polarographic reduction potential of aromatic compounds and is found by this method to be 4.5 ev or 103.5 kcal/mole. Therefore, the pathway which leads to the formation of excited 9-methylanthracene was unlikely.

While the compounds of the present invention contain significant chemical energy, they are not explosively unstable. Because of their stability, they are suitable for use in situations requiring a chemiluminescent compound which will not spontaneously decompose with the possibility of an explosion.

The activation energy of thermal decomposition of compound 1b is 29.3 kcal/mole in dimethylformamide.

This amount of energy corresponds to a half-life in solution of a few weeks at room temperature (25° C.). Compound 1b in a solid form has been stable without appreciable deterioration at 0° C. for a period exceeding one year.

The pericyclic association of energy-rich dimers of aromatic compounds with appropriate substituents represents a new type of chemiluminescence. These chemiluminescent compounds exhibit more desirable handling characteristics in the laboratory for mechanistic studies than the chemiluminescent peroxides, such as the dioxetanes. The synthesis and the thermolysis of these compounds containing electronegative substitutions on compound 1 are also expected to result in chemiluminescence.

The anthracene cyclodimers of the present invention bear electronegative substitutions at the bridgehead positions designated X and Y in FIG. 2a, also known as positions 9 and 10 of anthracene. These substitutions are electronegative substitutions which may be either inductive or resonant electronegative substitutions. Inductive electronegativity is an effect which is due to the tendency of an atom or a group of atoms to attract electrons. These electron-withdrawing inductive effects promote the chemiluminescence of the benzene:anthracene cyclodimers of the present invention.

The electronegative substitutions may also be of a resonant nature. The group of electrons forming the electronegative substituent group at the bridgehead positions on anthracene may be any group of electrons which are capable of two or more electronic arrangements whereby the electron is shared among the substituent atoms thereby increasing the stability of the electronegative substituent. This increase in stability is termed "resonance energy."

Among the electronegative substituents suitable for use in the present invention are: $-COOH$, $-N(CH_3)_3^+$, $-SO_3H$, $-CN$, F, Cl, Br or I; $-CO_2R$, $-SO_2R$, $-SOR$, wherein R is selected from the group consisting of aliphatic and aromatic groups; $-CZ_3$, wherein Z is Cl, Br or F; phenyl or substituted phenyl. When R is aliphatic it is a straight or branched chain hydrocarbon containing one to six carbons. When R is aromatic it is a phenyl or substituted phenyl where in 1 to 3 substitutions are made.

Chemiluminescence of the compounds of the present invention may be accomplished through energetic activation of the compound by any means capable of transmitting energy to the compound. Among the sources of activation are thermal energy, infrared energy, radiant energy, nuclear energy, electrical energy or chemical energy. A preferred source is thermal energy in the form of heat.

Additional preferred sources of energy are flash heating utilizing electricity or an infrared laser. The decomposition of the chemiluminescent compound produces substantial amounts of heat in addition to light. Therefore, the application of only a small quantity of energy is sufficient to trigger an autocatalytic decomposition reaction based upon the production of heat within the reaction itself.

The application of energy to the benzene:anthracene cyclodimers bearing one or two electronegative substitutions at the bridgehead positions X and Y results in the production of chemiluminescence. The actual amount of energy which must be applied to each individual compound can be readily determined using standard chemical procedures.

The compounds of the present invention are suitable for use in any situation requiring the production of light. Among the more preferred uses are the production of lasers utilizing the compounds of the present invention and an external energy source. The compounds of the present invention may also be used in a detection device for sensing the production of energy sufficient to stimulate detectible chemiluminescence.

The synthesis of the compounds of the present invention are illustrated in FIG. 2b and described in the Examples. The methods for the synthesis of the compounds of the present invention are substantially as previously described by Yang, et al. (1982). However, the previous method for producing an olefin required t-butyllithium which did not produce the compounds of the present invention. A novel method for the conversion of a 2-phenyl-1,3-dioxolane to an olefin requires reacting with potassium diisopropylamide in the presence of an aprotic solvent. Among the preferred aprotic solvents are the potassium salts of secondary amines and tetrahydrofuran (THF). The reaction of the potassium diisopropylamide with the 2-phenyl-1,3-dioxolane results in the production of an olefin as illustrated in FIG. 2b by compounds 1b or 1c.

Figure 3:
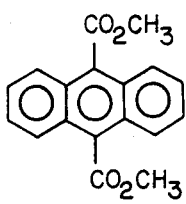
FIG. 3 illustrates the synthesis of 9, 10-anthracenedicarboxylic acid/benzene cyclodimers and their dimethyl esters, compound 1e.
Figure 3:
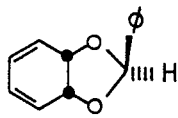
Figure 3:
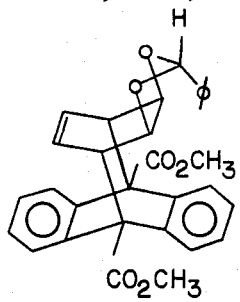
Figure 3:
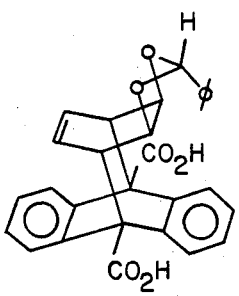
Figure 3:
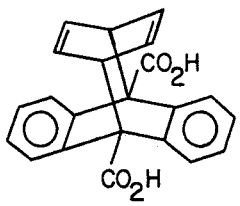
Figure 3:
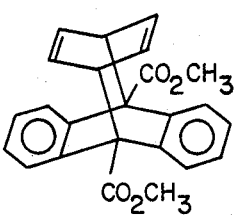

A compound of the present invention, with the X and Y substitution by $CO_2R$, where R is an aromatic or aliphatic hydrocarbon is illustrated in FIG. 3 and described in Example 5. In Example 5 the electronegative positions X and Y of compound 1 are both occupied by $CO_2CH_3$ to yield compound 1e.

In FIG. 3, compound 6 plus compound 3 are reacted with light from a mercury lamp filtered through a uranyl glass filter in methylene chloride at 0° C. To produce compound 4c. Compound 4c was dissolved in tetrahydrafuran and reacted with t-BuOK and water. Compound 5c was removed by ether extraction.

Compound 5c was reacted with potassium diisopropylamide (KDA) in dry tetrahydrafuran to produce compound 1c.

The diacid Compound 1c was dissolved in tetrahydrofuran and reacted with $CH_2N_2$/ ethanol to produce the diester compound 1e.

Similarly other aliphatic, straight or branched chain hydrocarbons, phenyl, or substituted phenyls, maybe substituted in place of the methyl group.

The present invention describes novel compounds and methods for their synthesis which are suitable for the production of light through a chemiluminescent reaction. This chemiluminescent reaction involves the direct conversion of chemical energy into light energy and can be initiated by the application of energy to the compound.

Although the foregoing invention has been described in some detail by way of illustration and example, for purposes of clarity and understanding, it will be obvious that certain changes and modifications may be practiced within the scope of invention.

For ease in discussion each compound will be given a number with a line under it. The following Table gives the systematic name for each of the intermediate compounds discussed or illustrated in FIGS. 2 and 3.

Compound 3: 2β-phenyl-8β,9β-dihydro-8,9-benzo-1,3-dioxolane.

Compound 4b: X=COOCH$_3$, Y=H: 2α-phenyl-1,3-dioxolane derivative of methyl 3β,4β-dihyroxy-3α,4α-dihydro-7,8,9,10-dibenzotricyclo[4.2.2.2$^{2,5}$]dodeca-7,9,11-triene-1-carboxylate.

Compound 4c: Y=COOCH$_3$: 2α-phenyl-1,3-dioxolane derivative of dimethyl 3β,4β-dihydroxy-3α, 4α-dihydro-7,8,9,10-dibenzotricyclo[4.2.2.2$^{2,5}$]dodeca-7,9,11-triene-1,6-dicarboxylate.

Compound 5b: X=COOH, Y=H: 2α-phenyl-1,3-dioxolane derivative of 3β,4β-dihydroxy-3α,4α-dihydro-7,8,9,10-dibensotricyclo[4.2.2.2$^{2,5}$]dodeca-7,9,11-triene-1-carboxylic acid.

Compound 5c: X=Y=COOH: 2α-phenyl-1,3-dioxolane derivative of 3β,4β-dihydroxy-3α,4α-dihydro-7,8,9,10-dibenzotricyclo[4.2.2.2$^{2,5}$]dodeca-7,9,11-triene-1,6-dicarboxylic acid.

EXAMPLE 1

Photocycloaddition of compound 3 to methyl 9-anthroate

This photocycloaddition reaction is illustrated in FIG. 2b. A solution of methyl 9-anthroate (0.26 g, 0.011 mole) and 3 (5.98 g, 0.03 mole) in 100 ml of dichloromethane was irradiated with a Hanovia 450-watt medium pressure Hg arc through a uranyl glass filter at −1°for 45 min. Another portion of methyl 9-anthroate (0.26 g) was added and the irradiation was continued for another 45 min. This process was repeated until a total of 2.6 g of the anthroate had been added. The solvent was then removed under reduced pressure. The residue was dissolved in dichloromethane and chromatographed over 120 g of silica gel. Adduct 4 was eluated from the column with a mixture of dichloromethane and petroleum ether (2:3). The yield was 4.22 g (88%). The product was recrystallized from CH$_2$Cl$_2$- hexane, mp 230°–231°, uv(CHCl$_3$), 257 (ε730), 263 (ε774), 270 (ε786) and 278 nm (ε868); ir(CH$_2$Cl$_2$), 3030, 2950 and 1733 cm$^{-1}$, nmr(CDCl$_3$) δ3.41 (1H, dd), 3.90 (3H, s), 4.20 (2H, s), 4.34 (1H, d), 5.67 (1H, t), 5.72 (1H, t), 5.95 (1H, s) and 6.92–7.27 (13H, m). Anal. Found: C, 79.88; H, 5.52.

EXAMPLE 2

The sponification of compound 4b to produce compound 5b.

This sponification reaction is illustrated in FIG. 2b. A solution of 4b (0.72 g) in 30 ml of absolute tetrahydrafuran (THF) was treated with a solution of potassium t-butoxide (t-BuOK) (1.69 g) in 10 ml of absolute THF containing 50 μl of water at 21°. After 2.2 hr, ice water was added to the solution and the mixture was extracted with CH$_2$Cl$_2$ (2×30 ml). The aqueous phase was acidified with CHl, and the mixture was extracted with CH$_2$Cl$_2$ (3×120 ml). The extract was washed, dried with MgSO$_4$ and evaporated. The residue was recrystallized from acetone:benzene to yield 0.63 g of 5 (91%), mp 252°. Compound 5b exhibits the following properties: uv(methanol), 265 (ε500), 256 (ε700), 250 (ε670), 243 nm (ε640; ir(CDCl$_3$), 3514, 3073, 3041, 2925, 1746 and 1706 cm$^{-1}$; nmr(DMSO-d$_6$), δ 3.36 (1H, m), 3.95 (2H, q), 4.26 (1H, d), 4.46 (1H, d), 5.57 (2H, m), 5.87 (1H, s) and 7.06–7.38 ppm (13H, m). Anal. Found: C, 80.08; H, 5.46.

EXAMPLE 3

Preparation of compound 1b

The preparation of compound 1b from compound 5b is illustrated in FIG. 2b. A solution of 5b (0.14 g) in 5 ml of absolute THF was treated with a solution of potassium diisopropylamide (KDA) in absolute THF (5 ml of 0.5 M solution) at 0°. After 30 min, the solution was treated with ice water and extracted with CH$_2$Cl$_2$ (3×30 ml). The aqueous phase was acidified with HCl at 0° and extracted with ether (3×60 ml). The ether extract was washed and dried with MgSO$_{34}$ and evaporated. The residue was recrystallized at low temperature from CH$_2$Cl$_2$ to yield 1b, 80 mg (80%), mp 80° and 219°, uv(ethanol) 285 (ε2900), 276 (ε 1830), 268 (ε1080), 255 (ε1520) and 222 nm (ε18200); nmr(CDCl$_3$), δ3.45 (1H, m), 4.35 (1H, d, J=10.5 Hz), 4.39 (1H, m), 5.83 (3H, m) and 7.08–7.13 ppm (8H, m); ms(CI isobutane): m/z 223, 205 and 179; (EI) m/z 222, 205, 177, 78 and very weak peaks at 300, 281 and 255.

EXAMPLE 4

The preparation of compound 1c and 1d

Compound 1c and 1d were prepared by similar methods as described in Examples 1, 2 and 3. Compound 1c exhibits the following properties: mp 90° and >255°; nmr(DMSO-d$_6$) 4.25 (2H, m), 5.63 (4H, m), 6.98 (4H, m) and 7.13 ppm (4H, m). Compound 1d exhibits: mp 110°–111°; uv(ethanol) 284 (ε2930), 276 (ε188), 270 (ε 1070, 255) (ε1450) and 220 nm (ε21200); ir(CCl$_4$) 3070–3025, 2974–2927 and 1685 cm$^{-1}$; nmr (CDCl$_3$) 1.95 (3H, s), 2.93 (1H, m), 3.48 (1H, m), 4.25 (1H, d, J=10.6 Hz), 5.84–5.89 (4H, m) and 6.98–7.28 ppm (4H, m).

EXAMPLE 5

Synthesis of photoadduct 4c

Cyclohexadiene 3 (4.194 g, 20.9 mmol) was dissolved in 100 ml of methylene chloride and placed in a photoreactor cooled to 0° in a cold bath. The first portion of dimethyl 9,10-anthracene dicarboxylate (ANDE 1), 1.102 g was added and the mixture degassed with argon for 25 min. The mixture was irradiated with a medium pressure Hanovia mercury lamp (450 W) through a uranyl glass filter for 50 min. Another portion of ANDE was added and the irradiation was continued for another 50 min. This procedure was repeated until a total of 2.368 g (8.05 mmol) of ANDE were consumed (Total Time 9.3 hr). Methylene chloride solvent was removed under reduced pressure to yield 7.670 g of yellowish residue, which was treated with cold methanol to give 3.450 g of colorless solid. The solid product mixture was further chromatographed over 150 g of silica (neutral, Activity I) with methylene chloride as the eluent. Photodduct 4c was obtained as a colorless solid, 2.621 g, 66% yield based on consumed ANDE. Photoadduct 4c was further recrystallized from dichloromethane hexane to yield colorless crystals, mp 228°–230° C. (dec.). uv(CH$_3$CN): λ$_{max}$(ε) 277 (474), 268 (566), 263 (549), 257 (445) nm. FT-IR(CH$_2$Cl$_2$: υ3034, 2952, 1736, 1605, 1478, 1226, 1084, 1065, 1037, 1026, 986, 975 966 cm$^{-1}$. 'HNMR(CDCl$_3$): δ7.22–7.15 (5H, m, φH), 6.99 (4H, m, ArH), 6.92 (4H, m, ArH), 5.92 (1H, s, φCH), 5.64 (2H, m, C=CH), 4.40 (2H, m, =CCH), 4.05 (2H, broad s, O—CH(C)), 3.90 (6H, s, CO$_2$CH$_3$) MS(EI, 10 eV): M/z 494 (1.8), 403 (5.1), 294 (100), 263 (74.2), 235 (12.6), 220, 204, 176. MS (CI, isobutane): M/z 495 (55.5), 496 (18.1), 497 (4.6), 389 (15.3), 295 (100).

Anal. calculated for C$_{31}$H$_{26}$O$_6$ (494.549): C, 75.29; H, 5.30. Found: C, 75.00; H, 5.30.

Hydrolysis of 4c to diacid 5c

Adduct 4c (0.500 g, 1.01 mmol) was dissolved in 25 ml of dry THF and the solution was added dropwise at 0° C. to a mixture of 2.075 g (18.5 mmol) of t-BuOK and 70 μl of H$_2$O (3.84 mmol) in 15 ml of dry THF. After 10 min of stirring at 0° C., the mixture was allowed to warm up to room temperature and stirring continued for 2.2 hr. The reaction mixture was then treated with 10 ml of water and extracted with dichloromethane (20 ml×2). The basic aqueous layer was acidified with concentrated HCl and extracted with diethyl ether (70 ml×3). The ether layers were combined and washed with saturated NaCl solution, dried (MgSO$_4$) and filtered. Removal of solvent under reduced pressure yielded a colorless solid compound 9: 0.456 g, 96.6%. An analytical sample of compound 5c was prepared by recrystallization from acetonebenzene, mp 282°–283° (dec.) uv(methanol): $\lambda_{max}(\epsilon)$ 264 (414), 254 (525), 249 (546), 244 (546), 214 nm (4900). FT-IR (CDCl$_3$): $\nu$2926, 2859, 1709, 1361, 1258, 1222, 1070, 597 cm$^{-1}$. 'HNMR (DMSO-d$_6$): $\delta$7.28–7.18 (13, m ArH), 5.92 (1H, s, $\phi$CH), 5.65 (2H, m, =CH), 4.39 (2H, m, =CCH), 4.07 (2H, broad s, OCH(C)). MS(EI): M/z 422, 378, 342, 316, 266, 249, 222, 205, 177.

Anal. calculated for C$_{29}$H$_{22}$O$_6$ (466.495): C, 74.67; H, 4.75. Found: C, 74.59; H, 4.77.

Synthesis of ANDA/BEN cyclodimer 1c

Cyclodimer 1c was prepared by treatment of 5c with KDA (potassium diisopropylamide). Adduct 5c (0.113 g, 0.242 mmol) was dissolved in 8 ml of dry THF and the solution was cooled in an ice-water bath. A freshly prepared KDA solution in THF (5.0 mmol in 7 ml of THF) was added dropwise under nitrogen with stirring. The mixture became cloudy and dark brown with color developing gradually. The mixture was further stirred at 0° for 50 min. Cold water was added to quench the reaction. Next the reaction mixture was taken into 50 ml of cold 0.5 N NaOH solution and extracted at 0° C. with dichloromethane (50 ml×2). The basic aqueous phase was acidified with cold concentrated HCl and the milky mixture extracted with diethyl ether (50 ml×3) and with ethyl acetate (50 ml). The combined organic layers were washed with cold brine, dried (MgSO$_4$) and filtered. The solid residue after removal of solvent at low temperature was treated with cold CH$_2$Cl$_2$ to give yellowish solid (77.8 mg, 75%). The solid was then further crystallized from CH$_3$OH at $-25°$ C. to give colorless crystals of compound 1c with the following properties: mp decomposition at ~90° C., apparent mp >300° C., 'HNMR(DMSO-d$_6$): $\delta$7.13 (8H, m, ArH), 5.63 (4H, m, =CH), 4.25 (2H, m, =CCH).

Preparation of ANDE/BEN cyclodimer 1e

Treatment of diacid 1c with CH$_2$N$_2$ in THF at 0° C. gave diester 1e. The yield was essentially quantitative. The product 1e was recrystallized from CHCl$_2$-hexane to afford colorless crystals, mp decomposition at ~78°, apparent mp 178°–180° C., 'HNMR(CDCl$_3$): $\delta$7.10 (4H, m, ArH), 6.83 (4H, m, ArH), 5.75 (4H, m, =CH), 4.36 (2H, m, =CCH), 3.90 (6H, s, CO$_2$CH$_3$).

The above Examples illustrate chemiluminescent compounds of the present invention. The critical substitution of electron-withdrawing groups on energy rich paracyclic benzene:anthrocin cyclodimers has been repeatedly demonstrated. These compounds are chemiluminescence compounds and result in the conversion of chemical energy into light energy during decomposition. The decomposition reaction may be triggered in many ways, particularly by the application of thermal energy thereby resulting in the release of a pulse of light.

The compounds of the present invention have been described and illustrated in the Examples. However, it will be appreciated that those skilled in the art, upon consideration of this disclosure, may make modifications and improvements within the scope of this invention.

I claim:

1. A composition of matter comprising compounds of the following structure:

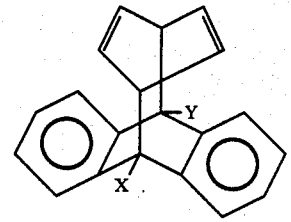

wherein X is hydrogen or an electron-withdrawing group; and

Y is hydrogen or an electron-withdrawing group; and no more than one of X and Y are hydrogen.

2. The composition of claim 1 wherein said Y is hydrogen and X is selected from the group comprising —COOH, —N(CH$_3$)$_3$$^+$, —SO$_3$H, —CN, F, Cl, Br, or I; —CO$_2$R, —SO$_2$R or —SOR, wherein R is selected from the group consisting of aliphatic and aromatic hydrocarbons; —CZ$_3$ wherein Z is Cl, Br, F; phenyl or substituted phenyl.

3. The composition of claim 1 wherein said X is hydrogen and Y is selected from the group comprising —COOH, —N(CH$_3$)$_3$$^+$, —SO$_3$H, —CN, F, Cl, Br or I; —CO$_2$R, —SO$_2$R or —SOR, wherein R is selected from the group consisting of aliphatic and aromatic hydrocarbons, —CZ$_3$ wherein Z is Cl, Br or F; phenyl or substituted phenyl.

4. The composition of claim 1 wherein said X and Y are selected from the group comprising —COOH, —N(CH$_3$)$_3$$^+$, —SO$_3$H, —CN, F, Cl, Br or I; —CO$_2$R, —SO$_2$R or —SOR, wherein R is selected from the group consisting of aliphatic and aromatic hydrocarbons; —CZ$_3$ wherein Z is Cl, Br or F; phenyl or substituted phenyl.

5. The composition of claim 4 wherein said X and Y are selected from the group consisting of —COOH, —N(CH$_3$)$_3$$^+$, —SO$_3$H, or —CN.

6. The composition of claim 4 wherein said X and Y are selected from the group consisting of F, Cl, Br, F or I.

7. The composition of claim 4 wherein said X and Y are selected from the group comprising —CO$_2$R, —SO$_2$R or —SOR wherein R is selected from straight or branched chain aliphatic hydrocarbons containing from 1 to 6 carbons.

8. The composition of claim 4 wherein said X and Y are selected from the group comprising aromatic hydrocarbons.

9. The composition of claim 4 wherein said X and Y are selected from the group comprising —CZ$_3$ wherein Z is Cl, Br, or F.

10. The composition of claim 4 wherein said X and Y are selected from the group comprising phenyl or substituted phenyl.

11. The composition of claim 2 wherein said X is —COOH.

12. The composition of claim 3 wherein said Y is —COOH.

13. The composition of claim 7 wherein said X and Y are COOCH$_3$.

* * * * *

UNITED STATES PATENT AND TRADEMARK OFFICE
CERTIFICATE OF CORRECTION

PATENT NO. : 4,883,898

DATED : 11/28/89

INVENTOR(S) : Nien-chu C. Yang

It is certified that error appears in the above-identified patent and that said Letters Patent is hereby corrected as shown below:

In column 1 after the title "Chemiluminescent Compounds" please insert the following on line 3:

--The United States Government has certain rights in the invention--.

Signed and Sealed this

Thirtieth Day of November, 1993

Attest:

BRUCE LEHMAN

Attesting Officer

Commissioner of Patents and Trademarks